(12) United States Patent
Turyansky et al.

(10) Patent No.: US 8,675,816 B2
(45) Date of Patent: Mar. 18, 2014

(54) X-RAY SPECTROMETER

(75) Inventors: Alexander Georgievich Turyansky, Moscow (RU); Mikhail Alexandrovich Negodaev, Moskovskaya obl. (RU); Roman Abramovich Khmelnitsky, Moscow (RU)

(73) Assignee: P. N. Lebedev Physical Institute of the Russian Academy of Sciences (LPI), Moscow (RU)

( * ) Notice: Subject to any disclaimer, the term of this patent is extended or adjusted under 35 U.S.C. 154(b) by 458 days.

(21) Appl. No.: 12/931,255

(22) Filed: Jan. 26, 2011

(65) Prior Publication Data

US 2011/0188631 A1     Aug. 4, 2011

(30) Foreign Application Priority Data

Feb. 1, 2010 (RU) .............................. 2010103135

(51) Int. Cl.
*G01T 1/36* (2006.01)
*G21K 1/06* (2006.01)

(52) U.S. Cl.
USPC .............................................. 378/85; 378/82

(58) Field of Classification Search
USPC ................................ 378/70, 82–85, 204, 210
See application file for complete search history.

(56) References Cited

U.S. PATENT DOCUMENTS 2,540,821 A * 2/1951 Harker ............................ 378/49
3,612,861 A * 10/1971 Dorfler ........................ 250/310
4,961,210 A * 10/1990 Fatemi ............................ 378/73
5,408,512 A * 4/1995 Kuwabara et al. ............... 378/45

FOREIGN PATENT DOCUMENTS

RU     2 217 732     11/2003

OTHER PUBLICATIONS

E. P. Bertin, Introduction to X-Ray Spectrometric Analysis, New York, Plenum Press, 1978, p. 88. (Spec, p. 1).
A. A. Rusakov, Radiography of metals. M., Atomizdat, 1977, p. 430. (Spec, p. 2).

* cited by examiner

*Primary Examiner* — Anastasia Midkiff
(74) *Attorney, Agent, or Firm* — Collard & Roe, P.C.

(57) ABSTRACT

The invention relates to X-ray spectral analysis and can be used for control of radiation spectra of X-ray generators as well as for analysis of elemental chemical composition and atomic structure of the specimens by measuring their absorption spectra. The X-ray spectrometer comprises at least one dispersing prism element, means of translation of the dispersing element relative to an X-ray beam, a refracted radiation detector and measuring tools for angle positioning of the dispersing element and the refracted radiation detector. The main distinction of the claimed spectrometer is that it contains an additional radiation detector, means to install it downstream the radiation reflected from the refracting surface of the dispersing element and measuring tools for its angle position in relation to the primary X-ray beam. The dispersing element is made of diamond, or beryllium, lithium hydride or boron carbide. The claimed spectrometer scheme provides a multiple increase of spectral measurements accuracy within the energy range up to 100 keV and possibility of pulse spectra calibration.

5 Claims, 3 Drawing Sheets

X-RAY SPECTROMETER

CROSS REFERENCE TO RELATED APPLICATIONS

Applicants claim priority under 35 U.S.C. §119 of Russian Application No. 2010103135 filed Feb. 1, 2010, the disclosure of which is incorporated by reference.

BACKGROUND OF THE INVENTION

1. Field of the Invention

This invention relates to X-ray spectral analysis and can be used for control of radiation spectra of X-ray generators as well as for analysis of chemical elements composition and atomic structure of specimens by measuring their absorption spectra.

The invention application is the most promising for study of fast processes kinetics when operating with modern high-power pulsed sources, for example with X-ray lasers, synchrotrons, and laser-electron sources on the basis of inverse Compton scattering.

2. The Prior Art

An X-ray spectrometer comprising a crystal dispersing element, translation means of a dispersing element relative to an X-ray beam and means for radiation detection is well-known (E. P. Bertin. Introduction to X-Ray Spectrometric Analysis. New York, Plenum Press, 1978.). The main disadvantage of that spectrometer is a low speed of spectrum measurements, as selection of spectral bands is provided in series by turning the dispersing element and the radiation detector relative to the analyzed X-ray beam. That spectrometer also precludes studying of fast processes in cases wherein conditions of the repeated measurements and exposure to radiation cannot be reproduced with high accuracy.

Also an X-ray spectrometer is known comprising a dispersing element in a form of a curved crystal, means of translation of a dispersing element relative to an X-ray beam and means of radiation detection (A. A. Rusakov. Radiography of metals. M., Atomizdat, 1977). A disadvantage of this spectrometer is connected with the fact that the spectrum measurement using this spectrometer can be provided only in case of sufficiently wide divergence of a primary beam. At the same time modern X-ray radiation generators have a narrow angle divergence, which is why measurements of direct radiation and broadband absorption spectra using the specified spectrometer are not possible.

An X-ray spectrometer comprising a prism dispersing element, means of translation of a dispersing element relative to an X-ray beam and means of radiation detection (Patent of RF No 2217732, G01N 23/04, 2002) is the closest to the claimed invention from the technical point of view. If a linear arrangement of serially located detectors is used as means of radiation detecting, this spectrometer provides feasibility of a full spectrum registration with a fixed position of a dispersing element. This allows to study the spectra in case of pulsed processes including a single X-ray shot if its power is sufficient for recording a signal with the specified noise-to-signal ratio (Patent of RF No 2217732, G01N 23/04, 2002).

The main disadvantage of this spectrometer is insufficient accuracy of absolute measurements of X-ray photon energies of the recorded spectrum. This disadvantage is caused by the fact that the angular spectrum of radiation dispersed by a prism depends strongly on the angular position of a prism relative to an axis of a primary X-ray beam. This angular position of a prism, however, can be uncontrollably changed as a result of a backlash of translation means of a dispersing element during adjustment procedure. The angular position of the said element may also drift due to heating by intense beam radiation. As a result a real angular position of the prism can substantially differ from a specified value. Furthermore, a primary radiation beam can have a significant cross-section width. This makes it difficult to determine the position of a prism refracting surface relative to the axis of a primary beam. It leads as well to inaccuracy in the angular coordinates determinations. All above mentioned factors cause significant errors of spectrum measurements and complicate the spectrometer adjustment.

SUMMARY OF THE INVENTION

The main objective of this invention is the increasing accuracy of spectrum measurements and simplification of adjustment of the spectrometer.

This problem is resolved by the following way. The X-ray spectrometer is proposed comprising at least one prism dispersing element, means of translation of the dispersing element relative to an X-ray beam, a refracted radiation detector and measuring instruments for angular position of the dispersing element and the refracted radiation detector. This spectrometer also contains an additional radiation detector installed downstream radiation reflected from the refracting surface of the dispersing element and instruments for measuring its angular position relative to the primary beam.

In addition, the claimed spectrometer contains devices for synchronization of measuring cycles of the refracted radiation detector and the additional radiation detector.

For the claimed radiation detectors the features for independent linear translation relative to the dispersing element and turning around the own axis that is perpendicular to the radiation incidence plane have been foreseen.

The prism dispersing element is made of one of the following materials such as diamond, beryllium, lithium hydride and boron carbide.

In the claimed spectrometer two dispersing prism elements and two refracted radiation detectors are included for which relative movements in direction that is perpendicular to the primary X-ray beam axis are foreseen.

The essence of the claimed invention is as follows. In case of grazing incidence of polychromatic radiation onto the flat interface of two media with different refraction indexes the X-ray beam is refracted, so that the angle of deviation of the refracted radiation from the original direction $\Delta\theta$ depends on radiation energy. Thus, the primary beam is divided into the refracted beam which diverges due to the radiation dispersion and the reflected beam. The angular position of the reflected beam is independent of the incident radiation energy and its angular divergence depends only on divergence of the primary beam. So, if the additional radiation detector recording the reflected radiation is installed in any specified time period the angular position of the refracting surface is measured at the same time with spectral measurements. This allows to correct the errors caused by drift of the measuring system parameters or uncontrolled change of the prism angular position that provides more accurate measurement of spectral data. This also eliminates the need in additional turns of the prism that simplifies adjustment of the spectrometer.

BRIEF DESCRIPTION OF THE DRAWINGS

Operation of the prism X-ray spectrometer is explained with FIGS. 1-6.

DETAILED DESCRIPTION OF PREFERRED EMBODIMENTS

Figure 1:
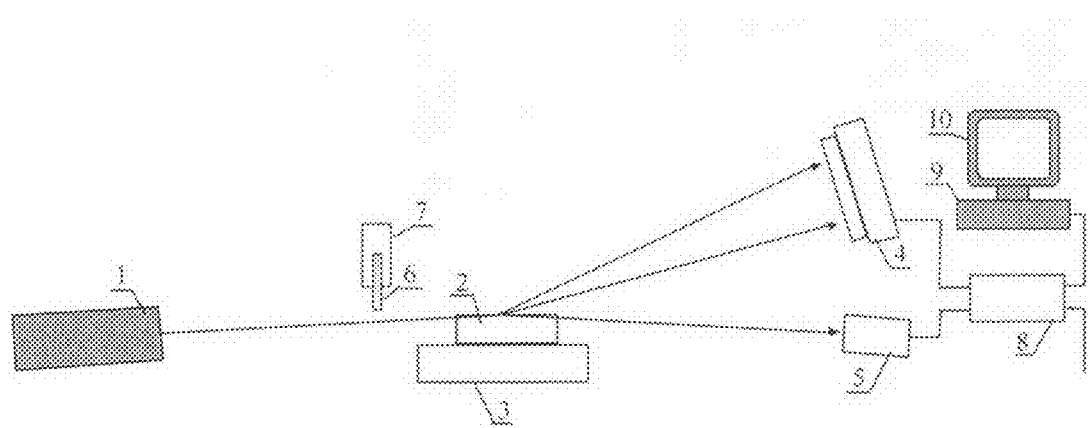
FIG. 1. General view of the X-ray spectrometer dispersion diagram

Operation of the X-ray spectrometer is explained with the diagram shown in FIG. 1. This diagram contains an X-ray source 1, a dispersing element 2 in form of a rectangular prism, means of translation 3 of the prism 2 relative to an X-ray beam, a refracted radiation detector 4, an additional detector 5, a sample under study 6, a holder 7 of a sample under study, an electronic unit 8 for the detected signals processing, a computer 9, a monitor 10. Elements 2-5 and 7-10 refer directly to the measuring scheme of the X-ray spectrometer. As a radiation source 1, powerful directed X-ray generators are used preferably, for example, an ondulator, a free electrons X-ray laser, a source based on the inverse Compton scattering effect containing a laser and an electron accelerator. For spectrometric measurements in the wide band the claimed sources can either sequentially change generated energy or the spontaneous part of the generated spectrum can be used. For measurements within the narrow energy band the natural width of the primary spectrum lines can be used.

Figure 2:
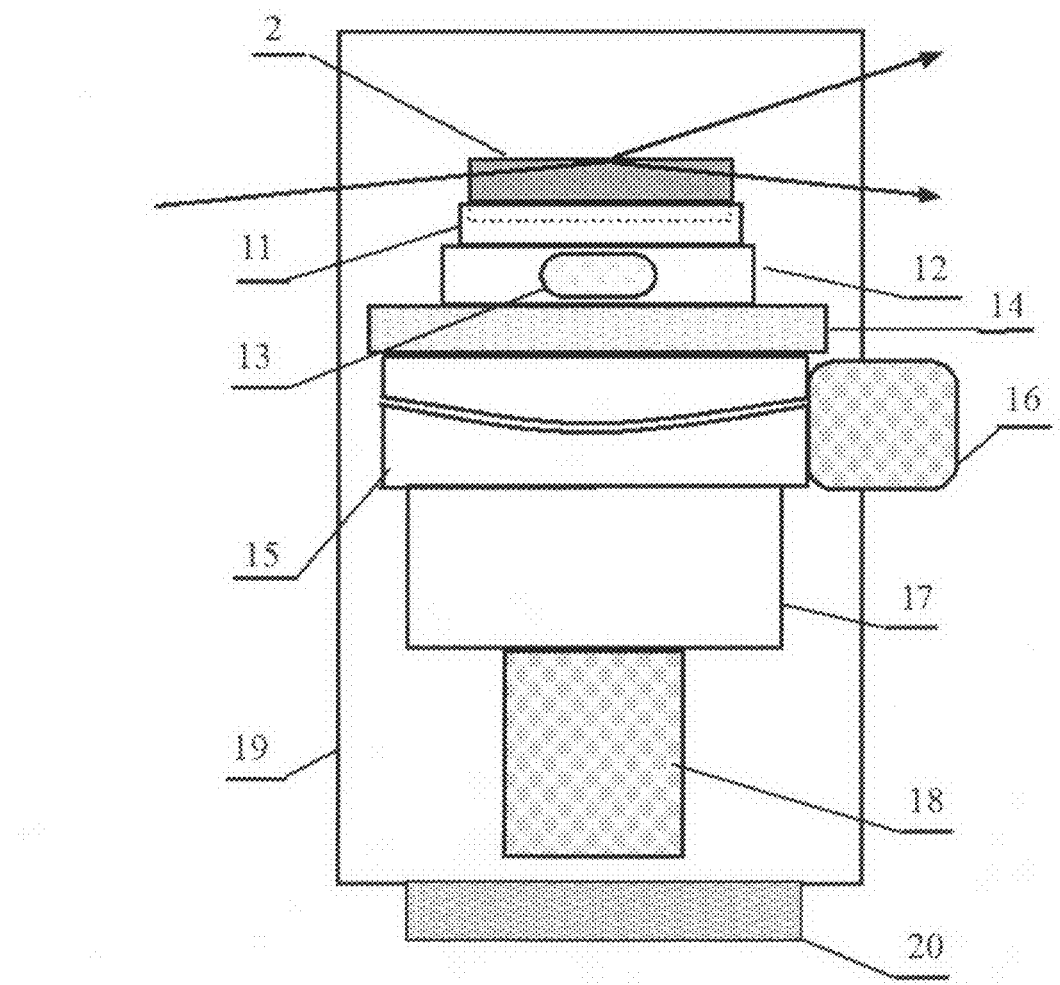
FIG. 2. The prism unit of the spectrometer

The prism 2 is made of monocrystal diamond in a form of a rectangular plate with flat surfaces. Means of translation 3 of the dispersing element relative to an X-ray beam (FIG. 2) comprise a holder 11 on which the prism 2 is located. The holder 11 is fixed on the heat-removing plate 12 connected through the cooling-transfer pipe 13 with the vessel filled with liquid nitrogen or other cooling liquid. The heat-removing plate 12 is placed on the thermal insulating gasket 14. The specified elements 2, 11-14 are located on the support pad of goniometer 15 providing setting and measurement of the specified angle of orientation of the refracting surface of the prism 2 relative to the axis of the primary X-ray beam. The goniometer rotation is provided with an electric drive 16. Elements 2, 11-16 are located on the pad of the linear translation device 17 containing the electric drive 18. The device 17 provides translations of the prism in the direction that is perpendicular to the axis of the primary X-ray beam. Elements 2, 11-18 are located on the support platform 19 for which feasibility of angular turning with an electric drive 20 is foreseen. Accurate position of the measuring plane relative to the base plane for example horizontal is provided by the way of rotation of the platform 19. $\pi/2$ turning allows also to analyze s- and p-polarized radiation reflected from the specimen surface. Application of the diamond prism provides the following advantages: 1) fast heat dissipation due to very high thermal conductivity of diamond, 2) quite low absorption of incident radiation due to a small atomic number of carbon (Z=6), 3) maximum angular dispersion, because diamond has maximum physical and electronic density ($\rho$=3,515 g/cm$^3$) among materials with small atomic numbers. In connection with high price of big crystals of natural diamond the prism can be made as a composite one of a few rectangular blocks with the specified crystallographic orientation, for example [110] or a plate of synthetic diamond produced, for example, by chemical precipitation from the gas phase. For recording the spectra in the range of low energies equal to ~1 keV the prism can be made, for example, of beryllium (Be), lithium hydride (LiH), boron carbide (B$_4$C).

For radiation detecting the coordinate-sensitive detectors are used, for example, on basis of strip structures made of silicon or gallium arsenide. In this case the strip period of the detector 4 recording the refracted radiation is selected on basis of condition $L_1\Delta\Theta_s \approx d_1$, where $L_1$ is a distance between the prism 2 and detector 4, $\Delta\Theta_s$ is an average angular width of the spectrometer instrumental function within the spectrum band under measurement. Strip period of the detector 5 recording the specular reflection is selected on basis of condition $d_2 \ll L_2\Delta\Theta_s$, where $L_2$ is a distance between the prism 2 and the detector 5. Distances $L_1$, $L_2$ are determined with using of the precision laser range finder. Observance of condition $d_2 \ll L_2\Delta\Theta_s$ for the detector 5 provides high accuracy of measurement of the reflected radiation angular position. In case of $d_1 \sim d_2$ observance of the specified requirements is provided by moving away the detector 5 from the prism 2; in case of $L_1 \sim L_2$ it is provided by decreasing the period $d_2$.

Figure 3:
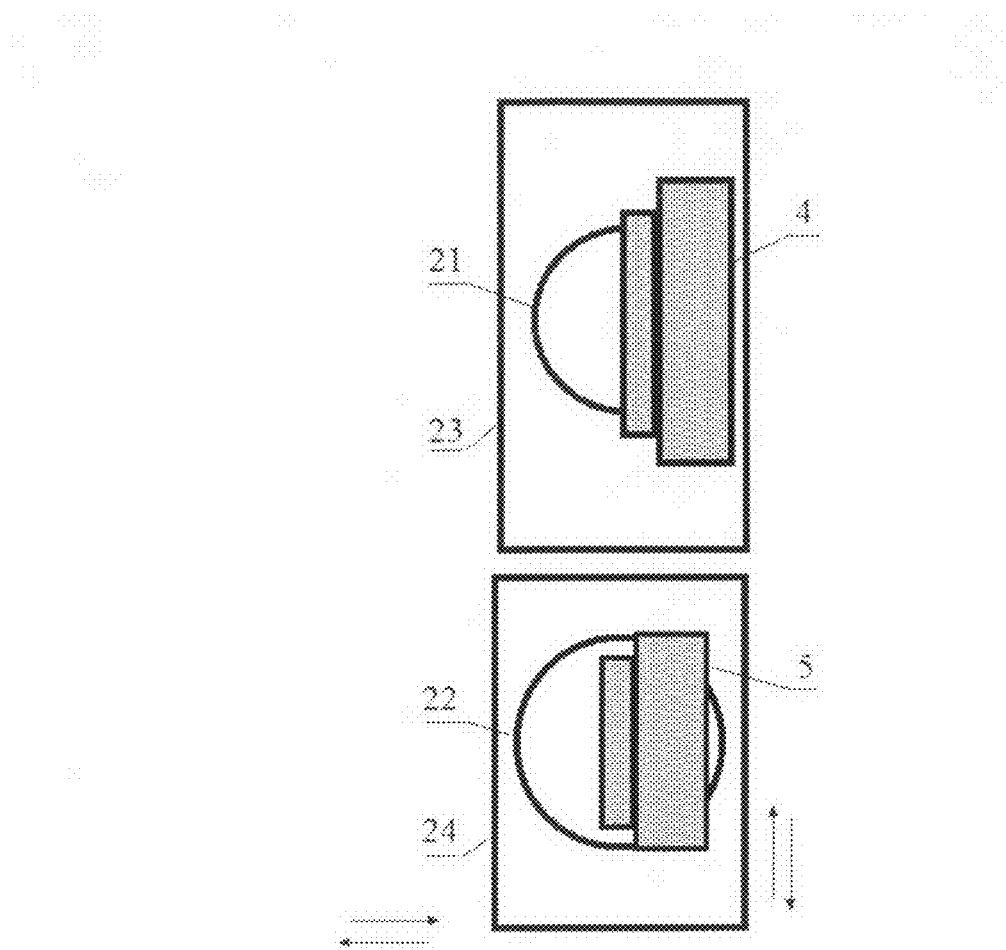
FIG. 3. The refracted and mirrored radiation detecting units

Strip detectors 4, 5 are located on the goniometer rotational platforms 21, 22 (FIG. 3). The rotational platforms 21, 22 with the strip detectors 4, 5 can be moved perpendicularly to the axis of the primary X-ray beam (vertical arrows) with use of the precision linear translation systems 23, 24. The precision linear translation precision systems 23, 24 are also devices for angular movement and measurement of the angular position of the refracted radiation detector 4 and the additional detector 5. The platforms 21, 22 also can be moved independently along the axis of the beam (horizontal arrows). The specified movements provide change of angular aperture and width of the spectral band correspondingly recorded by the detector 4. In case of fixed accuracy of the linear translation systems 23, 24 an increase of distance between the dispersing element and the radiation detector allows to enhance accuracy of determination of angular coordinates of the radiation detectors 4, 5. Movements of elements 21-24 is provided by commands of the computer 9.

When the pulse source generates X-ray radiation the spectrometer operation is provided according to the following procedure. The cooling system of the prism 2 starts up. The specified angular position of the refracting face of the prism 2 relative to the axis of the primary X-ray beam generated by the source 1 is adjusted by the command from the control computer with use of goniometric device of means of translation 3. The detectors 4 and 5 are installed in the position when the central sensitive parts of their active region coincide approximately with the expected calculated positions of the refracted and reflected beam intensity peaks. A zero angular coordinate is specified preliminarily by the position of the direct radiation maximum peak. This procedure is used for the narrow directed X-ray beam. If a cross-section of the primary beam is larger than a cross-section of the beam intercepted by the refracting face of the prism 2 at a small grazing angle the zero point is determined by the following way. The prism refracting face is placed at grazing angle $0<\theta<\theta_{mc}$, where $\theta_{mc}$ is a critical angle of full external reflection of minimum spectral energy. With prism 2 entering into the X-ray beam in the recording plane behind prism 2 two zones of radiation intensity are observed such as a direct radiation zone and a zone of radiation impaired after passing through the prism. These zones are separated by the intensity minimum as with the specified position of the refracting face it deflects (screens) fully a part of incident radiation flux. The minimum point recorded by detectors 4, 5 is selected as a control zero point of the detectors linear coordinate relative to the primary X-ray beam in the plane that is perpendicular to its axis. As mentioned above under condition $d_2 \ll L_2 \Delta \Theta_s$ determination of a zero point by the additional detector 5 is more accurate.

Recording and processing of signals from detectors 4 and 5 is provided according to the following procedure. Electronic unit 8 picks up the external synchronization signal from the control system of radiation source 1. Under this signal the primary amplifying channels (preamplifiers) of radiation detectors 4, 5 are opened. The electric signals generated by X-ray photons in the detecting elements of detectors 4, 5 are amplified, multiplexed and digitized with fast A/D converters and transferred to the control computer 9 where they are stored. At that condition $T_s < T_p$, is fulfilled where $T_s$ is a full time of processing, transferring and storing of all signals of the detecting elements, $T_p$ is a pulse period or minimum time between X-ray pulses of the radiation source 1.

The integral value of signals $I_s$ of all detecting elements of detector 5 allows to determine the radiant power of primary radiation falling upon the prism front face using the following expression:

$$P_0 = \frac{I_s}{R(\theta, E)\exp[-\mu_c(E)L]\eta(E)} \quad (1)$$

R is a coefficient of reflection from the refracting face of prism 2, $\mu_c$ is a linear absorption coefficient of prism 2, $\eta$ is a recording efficiency of the incident radiation detector 5, L is a length of the refracting face of prism 2, $\theta$ is a grazing angle of a beam falling on the refracting face of prism 2, E is X-ray photon energy.

Values of the parameters can be determined previously before the specimen introduction and angular parameter $\theta$ is found under the gravity center point of the curve of specular reflection from the prism refracting face that is recorded by the detector 5. In case of quite a narrow spectrum band $\Delta E/E < 10^{-2}$ the average energy value can be used for calculation. In the wide spectral band it is necessary to use the spectrometric data obtained with detector 4. Determination of value $P_o$ allows to provide continuous calibration of the X-ray source pulse power. In case of generation of powerful pulse radiation the power of single impulses can fluctuate greatly, at that, the range of relative power variations reaches $\pm(1 \div 10)$%. If the pulse reflected from prism 2 recorded by the detector 5 contains, for example, more than $10^6$ photons, statistic fluctuations of radiation flux are lower than 0.1% and can be neglected. In this case the specified calibration procedure decreases errors of absolute absorbed spectrum measurement results not lower than by order of magnitude.

Figure 4:
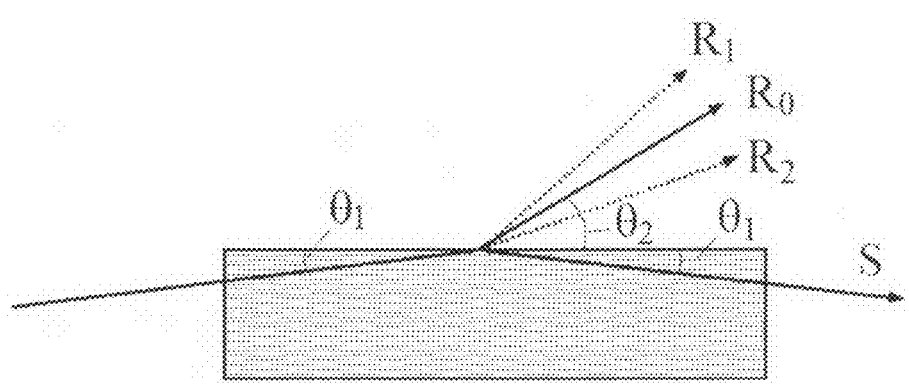
FIG. 4. Diagram of refraction and mirroring on the prism refracting surface

Within the frame of approaching of ray optics for weakly absorbing mediums for the diagram shown in FIG. 4 the angular position of the refraction peaks is determined by the following expression:

$$\Psi = \sqrt{\theta_1^2 + 2\delta(E)} - \theta_1, \quad (2)$$

where $\Psi$ is an angle of the refracted beam deflection from the primary beam direction, $\theta_1$ is an grazing angle of the primary beam relative to the refracting surface, $\delta$ is a real part of the prism material refraction index decrement that is a function of incident radiation energy E. In FIG. 4 rays $R_1$ and $R_2$ meet the minimum and maximum spectral energy values. $\theta_2$ is a refraction angle of the beam whose energy corresponds with the point of gravity of the spectral distribution indicated by ray $R_0$. The advantage of the pattern of the beam entering through the front face oriented approximately perpendicular to the axis of the direct beam is connected with the fact that with the specified orientation the prism angular magnification coefficient <1 and therefore, influence of the primary beam divergence on spectral resolution is minimal.

Values $\delta(E)$ normalized to the unit density were tabulated and stored in the computer memory. So using known values $\delta(E_i)$ and resolving numerically the equation (2) by computer calculation the incident radiation spectrum is determined under the experimental set of values $\{\Psi_i\}$. The angle of deviation of $\Psi_i$ is determined by the following expression:

$$\Psi_i = \Psi_o + (i-j)d_1/L_1 \quad (3)$$

where j is a number of a reference strip, whose position corresponds with angle of $\Psi_o$, specified by movement of the detector 4 by commands from the computer 9, i is a current number of the radiation detector strip. Because of smallness of deviation angles of X-rays refracted in the prism 2 the expression (3) provides determination of $\Psi_i$ with relative error that is lower than 0.01%. The angle $\theta_1$ is found from ratio $(s_1-s_2)/L_2$, where $s_1$, $s_2$ are, correspondingly, linear center coordinates of the direct beam determined during adjustment and of the reflected beam. These coordinates are measured from data recordings of the detector 5. Variations of the value of $\theta_1$, caused, for example, by radiation heating of the dispersing element or set by the program controlling computer 9 are measured by the detector 5 and stored in memory for the subsequent program processing of a spectrum.

Figure 5:
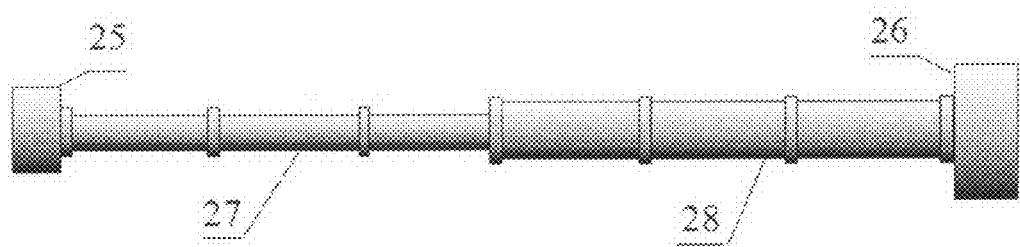
FIG. 5. General view of the X-ray spectrometer

For effective spectrometer operation it is necessary to provide spatial separation of the dispersing system with a prism and the radiation detectors by distance more than 1 m, and for precision measurements it should be more than 10 m. In connection with this fact for elimination of absorption and dispersion in air the key elements of the spectrometer should be located in a vacuum system. In FIG. 5 the general view of the spectrometer is shown that comprises vacuum chambers 25, 26, where the following devices are installed: the prism 2 with the means of its translation and the refracted radiation detector 4, and the additional detector 5 with the means of its translation. Vacuum chambers 25, 26 are connected by vacuum pipe consisted of sections 27, 28 of different diameters. The increase of section diameters provides passing of the divergent radiation beams reflected and refracted by the prism 2.

Figure 6:
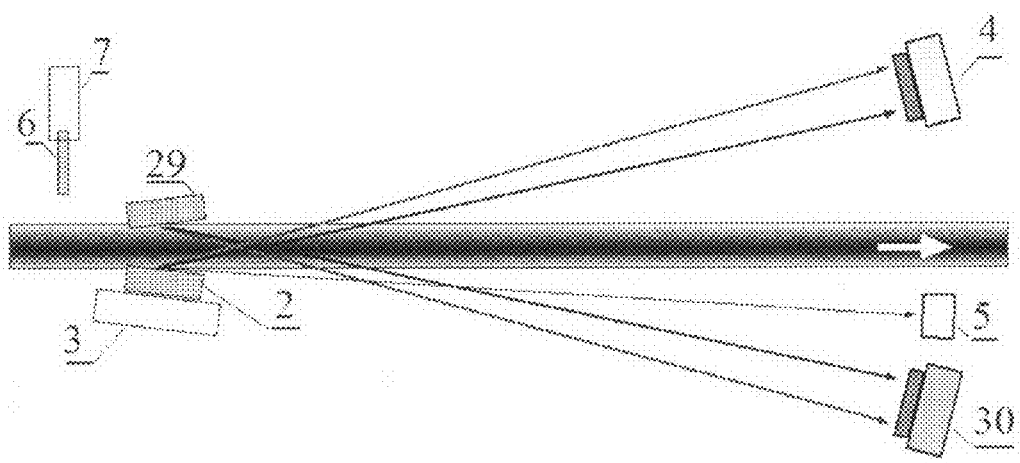
FIG. 6. The spectrometer scheme with two spectrometric channels.

In case of high power of an X-ray source the X-ray beam jitter effect connected with random drift of the beam axis and intensity peak from pulse to pulse can appear. In particular, for the free-electron X-ray laser such drift may reach ~10% of the value of the beam cross-section diameter. In this case for reliable calibration of the X-ray beam parameters the spectrometer scheme shown in FIG. 6 can be used. The scheme contains two dispersing elements 2 и 29 made in a form of a rectangular prism and two refracted radiation detectors 4 and 30. The elements 2, 29 and 4, 30 are located at opposite sides of the X-ray beam with feasibility of relative movement in direction that is perpendicular to the beam axis. So, by comparison of signal intensities of the refracted radiation detectors 4, 30, installed at edges of the primary beam the value of the beam axis drift can be determined and the more accurate calibration of the X-ray pulse power integral value can be provided.

The claimed invention can be realized on the base of meteorological equipment produced serially. The proposed engineering solution provides a multiple increase of accuracy of absolute X-ray spectrum measurement results as well as capability of continuous calibration of the primary spectra. In the claimed device the accuracy of determination of the prism angular coordinate is provided by width of the additional radiation detector strip. In particular, with the strip width of 10 μm and with an error of determination of the prism position relative to the beam axis equal to 50 μm, accuracy of angular measurements and correspondingly, accuracy of the radiation energy measurements increase approximately five times. Elimination of additional turns of the prism simplifies the spectrometer adjustment essentially.

Application of the claimed spectrometer is the most promising for monitoring of the primary X-ray spectra in the range of energies 5-100 keV generated by powerful pulse sources and for determination of absorption spectra of specimens under study. With synchronization of external action on the object under study and time of X-ray pulse generation the claimed spectrometer provides feasibility of fast processes investigations in different materials using a single radiation shot.

What is claimed is:

1. An X-ray spectrometer comprising
   at least one dispersing prism element,
   means of translation of the dispersing prism element relative to an X-ray beam,
   a refracted radiation detector and measuring tools for angle positioning of the dispersing prism element and the refracted radiation detector,
   an additional radiation detector installed downstream from radiation reflected from a refracting surface of the dispersing prism element, and
   additional measuring tools installed for displacement determination of the additional radiation detector.

2. The X-ray spectrometer according to claim 1,
   wherein means for synchronization of measurement cycles of the refracted radiation detector and the additional radiation detector is included.

3. The X-ray spectrometer according to claim 1,
   wherein both said radiation detectors have the translation means for independent linear movements relative to the dispersing prism element and rotation means for angular movements relative to an axis normal to a plane of radiation incidence.

4. The X-ray spectrometer according to claim 1,
   wherein the dispersing prism element is made of one of the following materials: diamond, beryllium, lithium hydride or boron carbide.

5. The X-ray spectrometer according to claim 1,
   wherein the additional dispersing prism elements and the additional refracted radiation detectors are installed, and for said radiation detectors there are linear translation means in a direction perpendicular to a primary radiation beam axis.

* * * * *